(12) United States Patent
Wolpert et al.

(10) Patent No.: US 6,622,662 B1
(45) Date of Patent: Sep. 23, 2003

(54) ADAPTER FOR VAPORIZING DEVICES

(75) Inventors: Christopher J. Wolpert, Scottsdale, AZ (US); Scott Allen Richert, Peoria, AZ (US); Phillip Scott Bradley, Avondale, AZ (US); Donald R. Richardson, Scottsdale, AZ (US)

(73) Assignee: The Dial Corporation, Scottsdale, AZ (US)

( * ) Notice: Subject to any disclaimer, the term of this patent is extended or adjusted under 35 U.S.C. 154(b) by 0 days.

(21) Appl. No.: 10/167,827

(22) Filed: Jun. 12, 2002

(51) Int. Cl.[7] ................................................ F22B 37/18
(52) U.S. Cl. ........................ 122/366; 392/390; 392/395; 392/403
(58) Field of Search ................................. 122/4 R, 366; 392/390, 394, 395, 392, 403; 219/542, 545

(56) References Cited

U.S. PATENT DOCUMENTS

| | | | | |
|---|---|---|---|---|
| 5,038,394 A | * | 8/1991 | Hasegawa et al. | 392/395 |
| 5,290,546 A | * | 3/1994 | Hasegawa et al. | 424/76.2 |
| 5,647,053 A | * | 7/1997 | Schroeder et al. | 392/390 |
| 5,971,369 A | * | 10/1999 | Neveu et al. | 261/91 |

* cited by examiner

Primary Examiner—Gregory Wilson
(74) Attorney, Agent, or Firm—Snell & Wilmer LLP

(57) ABSTRACT

An adapter system for vaporizing devices is provided. In general, the adapter system couples to a refill bottle unit or container and includes an attachment mechanism and a shape-altering mechanism. Essentially, a refill bottle unit that otherwise would not properly fit into a housing unit of a vaporizinrg device is modified by the adapter system to now properly fit and function normally within the housing unit. Alternatively, the adapter system may modify the housing unit for receipt of a non-conforming bottle unit.

14 Claims, 6 Drawing Sheets

ADAPTER FOR VAPORIZING DEVICES

FIELD OF THE INVENTION

The invention generally relates to vaporizing devices. More specifically, the invention relates to an adapter for vaporizing devices.

BACKGROUND OF THE INVENTION

Electric liquid vaporizers are generally known and typically comprise a housing unit configured to receive a liquid container or bottle portion. In such systems, the liquid container usually includes some form of liquid transport system. For example, a wick partially immersed in the liquid permits the liquid to be transported through the wick by capillary action. A heater unit is generally used to promote or encourage vaporization of the liquid from the wick. As such, proper positioning and placement of the liquid container and wick with respect to the housing unit enables optimal performance of the vaporizer system. In this sense, the system may include certain features to promote proper fit of the container within the housing unit. For example, the container may be threaded and engaged within the housing unit in a screw-like manner, or the container may be interconnected to the housing unit in a "snap-and-fit" manner.

Numerous liquid vaporizing systems and methods for interconnecting a bottle unit to a housing unit have been developed and are known. One drawback of these prior art systems is that the bottle units are typically uniquely shaped to fit into a single corresponding housing unit, and similarly, the housing unit will generally only receive this uniquely shaped bottle unit.

With reference now to FIG. 1, an example of one type of a liquid vaporizer system and method for interconnecting the bottle unit and housing is illustrated. In this illustrative example, an electric liquid vaporizer 10 is shown to include a specifically configured housing unit 12 and a specifically configured refill bottle unit 14. This vaporizer 10 is one embodiment of the invention disclosed in U.S. Pat. No. 6,104,867 issued Aug. 15, 2000 to Stathakis et al., the entire contents of which are incorporated herein by reference. It should be recognized that housing unit 12 is shown from a perspective frontal view while bottle unit 14 is shown from a back view. Housing unit 12 includes a front surface 20 extending to a back surface 22 surrounding a cavity 26. Cavity 26 within housing unit 12 is suitably sized and configured to receive and retain bottle unit 14. Bottle unit 14 includes a wick 40 which preferably extends the length of bottle unit 14 to facilitate transportation of substantially all of the liquid contained within. This particular embodiment further includes a bottle guidance system comprising a protrusion 70 within cavity 26 and a corresponding recess 72 on bottle unit 14. The back wall of bottle unit 14 includes recess 72 which may include an enlarged upper opening 74 to aid in aligning bottle unit 14 to housing unit 12 and specifically, protrusion 70 to the lower portion of recess 72. In this manner, as bottle unit 14 is disposed within cavity 26, protrusion 70 aligns with recess 72 to secure the bottle unit within the housing. Thus, housing unit 12 and bottle unit 14, in a unique combination, fit together to form the liquid vaporizer system.

From this description, for example, it should be appreciated that the housing unit/cavity of the liquid vaporizer system shown in the '867 patent is not particularly conducive to accepting bottle units, for example of other liquid vaporizer systems that do not include at least some of the features of bottle unit 14 disclosed therein.

Unfortunately, attempts to forcibly insert a non-conforming refill bottle unit into a uniquely shaped housing unit may result in poor or unsatisfactory operation of the vaporizer system and/or damage or breakage of the system. On the other hand, the intermixing of housing units of one vaporizer system with a bottle unit from another vaporizer system may offer various advantages. For example, only one brand of a refill unit may be available at a particular market, the fragrance of a non-conforming refill unit may be desired, or the consumer may simply forget which brand of liquid vaporizer the consumer has previously purchased (for example, in most instances consumers will not bring the warmer unit, e.g. housing unit 12 of the '867 patent, with them on their shopping excursions). Any number of these or other issues may result in a consumer having a refill unit that does not fit into the housing unit of the vaporizer system they may wish to use.

Thus, there exists a need for an apparatus, system and method of disposing a liquid container or refill bottle unit into a housing unit, regardless of the shape of the bottle unit, housing unit or both. Additionally, there exists a need for an apparatus which, when used in combination with a typical vaporizing device, permits intermixing of variously shaped bottle units with nonconforming housing units, and vice versa.

SUMMARY OF THE INVENTION

The present invention, in general, addresses these and other needs by providing an apparatus, system and method of vaporization including an adapter system. While the particular adapter may vary in shape, size and configuration, in accordance with various embodiments of the present invention the adapter system comprises a shape-altering mechanism to permit disposition of a non-conforming container within a housing unit of a vaporizing device.

A vaporizer system of the invention generally includes a bottle unit, a housing unit having a cavity for receipt of the bottle unit, and an adapter system having an attachment mechanism and a shape-altering mechanism. Preferably, the adapter system is advantageously configured to fit between the bottle unit and the housing unit either by, coupling to the container prior to disposition, coupling to the housing unit, or otherwise.

A refill bottle system of the invention for use in vaporizing devices generally includes a liquid container and an adapter system coupled to the container. The adapter system alters the shape of the container to permit the otherwise non-conforming container to be used in the vaporizing device.

In one embodiment, the adapter includes a body portion, a neck portion and a pliable section formed there between. The pliable section permits the body portion to contact a side of the container.

One method of vaporization according to the invention, generally includes appending an adapter system to a container and disposing the container and adapter system within a housing unit of a vaporizing device. The adapter system modifies the shape of the container to permit the disposition. In a particular embodiment of the method, the container and adapter system is removed from the housing unit and the adapter system can be removed from the container.

BRIEF DESCRIPTION OF THE DRAWINGS

The subject matter of the invention is particularly pointed out and distinctly claimed in the specification. A more complete understanding of the invention may best be obtained by referring to the detailed description and claims in connection with the drawing figures, wherein like numerals designate like elements, and:

DETAILED DESCRIPTION OF EXEMPLARY EMBODIMENTS

Figure 1:
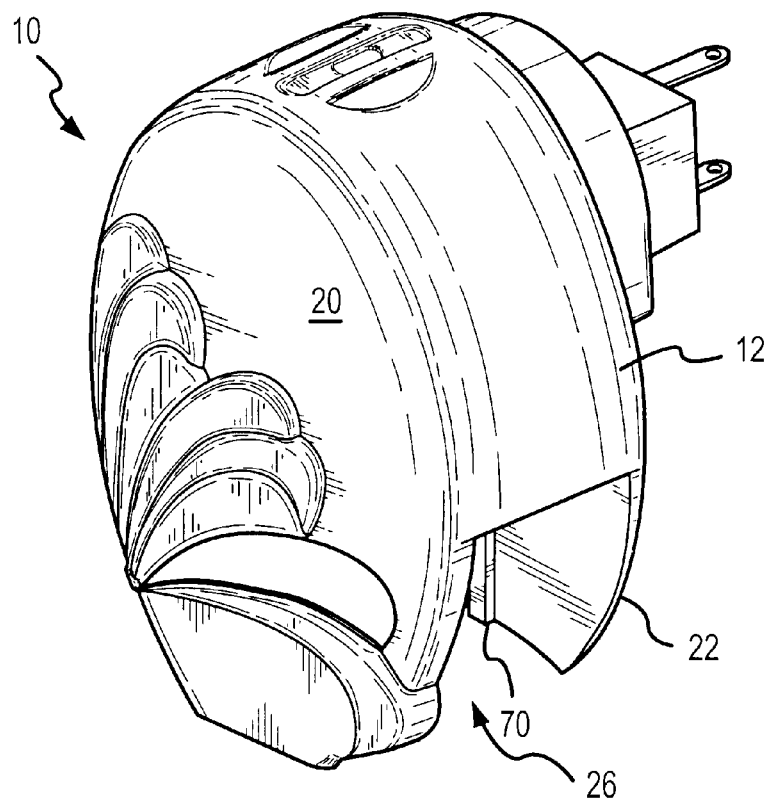
FIGS. 1 and 2 illustrate exploded views of the electric liquid vaporizer disclosed in U.S. Pat. No. 6,104,867 issued Aug. 15, 2000 to Stathakis et al., wherein FIG. 1 corresponds to FIG. 7 of the '867 patent and illustrates a housing unit, and FIG. 2 corresponds to FIG. 6 of the '867 patent and illustrates a bottle unit.

The subject matter of the invention is particularly suited for use in connection with vaporizing devices, such as those typically used in connection with liquid containers or refill bottle units and housing units. As a result, the following exemplary embodiments of the invention are conveniently described in that context. It should be recognized, however, that such description is not intended as a limitation on the scope, use, applicability or configuration of the invention. Rather, the following description is provided merely to enable a full and complete description of certain disclosed embodiments. As will become apparent, various changes may be made to the elements described without departing from the scope of the invention.

A universal adapter for vaporizing devices, and a method for liquid vaporization utilizing the same, according to various aspects of the invention is disclosed. Generally, a refill bottle system of the invention includes a liquid container or refill bottle unit and a universal adapter system. In various exemplary embodiments, the adapter system generally includes an appending or attaching mechanism for securing the adapter between the liquid container and a housing unit, and a shape-altering means configured to vary the container and/or the housing shape to permit proper fitting of the container unit within the housing unit, regardless of the original container shape. In addition, an adapter system according to various embodiments of the invention may be configured to removably append to a liquid container to permit fitting into multiple variously configured housing units.

An adapter system in accordance with the principles of the invention generally includes a shape-altering mechanism. The shape-altering mechanism alters, modifies, varies or otherwise adapts a typical vaporization system to permit the intermixing of a nonconforming container unit with a housing unit. As will be described in further detail, the housing unit, and in particular the cavity of the housing unit, may be shape-altered or the container unit may be shape-altered.

In addition, an adapter system in accordance with the principles of the invention may further include an attachment mechanism. The attachment mechanism appends, adheres, couples or otherwise joins the adapter system to a typical vaporization system to stabilize the adapter system with the vaporization system. As will be described in further detail, the adapter system may be combined with the container unit or with the housing unit prior to the connection between the container unit and the housing unit.

With reference to the schematic diagrams variously set forth in FIG. 3 the problems created by the aforementioned prior art and the various solutions provided in accordance with various aspects of the present invention are demonstrated. For example, FIGS. 3A and 3B are illustrative of two prior art vaporizer systems each comprising a container unit (e.g. container units A and B) and a housing unit (e.g. housing units A and B). The FIGS. illustrate, such as by the arrow, that container unit A fits into or is otherwise interconnected with housing unit A to form vaporizer system A, e.g., a generally known electric liquid vaporizer. Inasmuch as the operation of vaporization systems of this type are generally known to those of skill in the art, a detailed description of the operation will not be described herein. As is common in vaporizer systems, the interconnection of container unit A with housing unit A results in a complete vaporizer system A. In a similar manner, vaporizer system B of FIG. 3B includes a container unit B and a housing unit B which, when interconnected, form a complete vaporizer system B. In general, vaporizer or vaporization systems A and B may be similar in operation; however, container units A and B, and housing units A and B, are generally not the same shape and size.

Figure 3A:
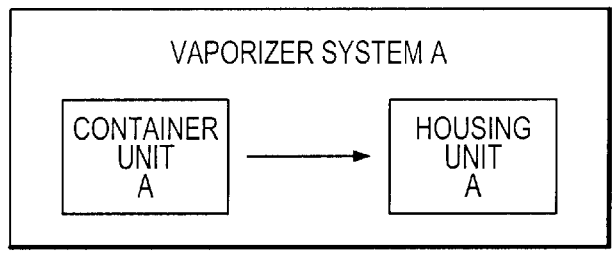
FIGS. 3A–3D are block diagrams of conventional vaporizer systems.
Figure 3B:
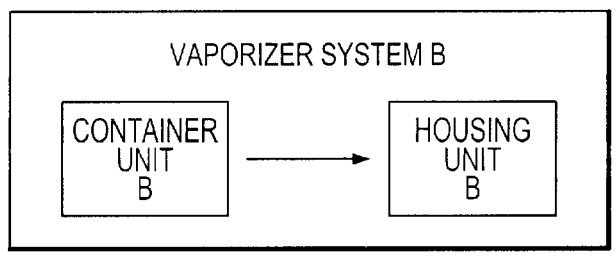
Figure 3C:
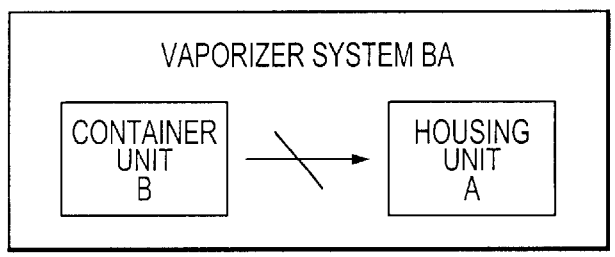
Figure 3D:
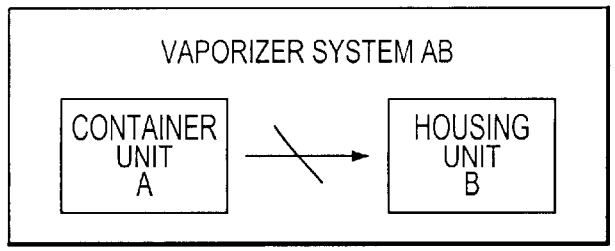

With reference to FIG. 3C, as shown by the broken arrow, container unit B does not fit into housing unit A, and thus, it is not possible to form a vaporizer system BA with container unit B and housing unit A. In fact, FIG. 3C shows that container unit B will not properly fit into housing unit A because, for example, container unit B is not shaped to fit within housing unit A, housing unit A is uniquely shaped to receive a container shaped similar to container unit A, or a combination of both. FIG. 3D shows, in a similar manner, that container unit A will not properly fit into housing unit B for the same or similar reasons, to form a vaporizer system AB. Thus, as is commonly known, intermixing of container units among various housing units of different vaporizer systems is generally not available.

Figure 3E:
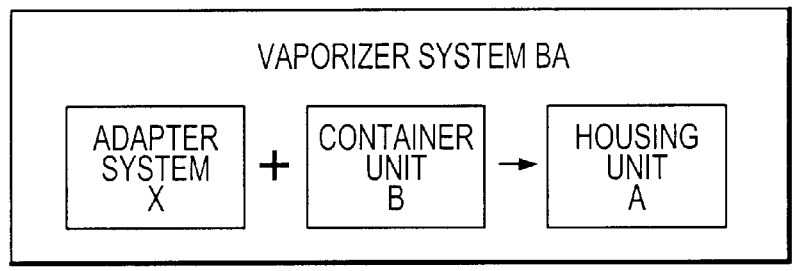
FIGS. 3E–3H are block diagrams of conventional vaporizer systems in combination with an adapter system of the invention.
Figure 3F:
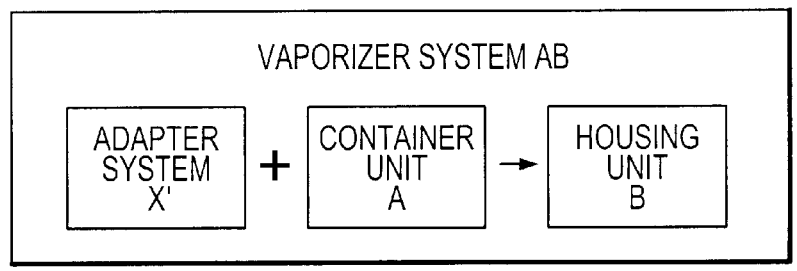

FIGS. 3E–3H show the same or similar conventional vaporizer systems as demonstrated in FIGS. 3A–3D, except that the various vaporization systems are in combination with an adapter system X in accordance with the principles of the invention. As previously shown in FIG. 3C, container unit B will not properly fit into housing unit A to form vaporizer system BA; however, as shown in FIG. 3E, when container B is combined with an adapter system X having shape-altering means, the original configuration of container unit B is modified so now container unit B can be disposed within housing unit A and a complete vaporizer system BA is formed. Similarly, FIG. 3F demonstrates that the inclusion of an adapter system X' of the invention, permits container A to fit within housing unit B, which previously did not form a proper fit as illustrated in FIG. 3D. It should be recognized that the same adapter system in accordance with one embodiment of the invention may be configured to permit variously shaped containers, such as container units A and B, to fit into variously shaped housing units, such as housing units A and B. Alternatively, an adapter system may be configured to permit a particularly shaped container, such as container B, to fit into a particularly shaped housing unit, such as housing unit A. Thus, an adapter system of the invention may be versatile or unique depending upon the particular use or application.

Figure 3G:
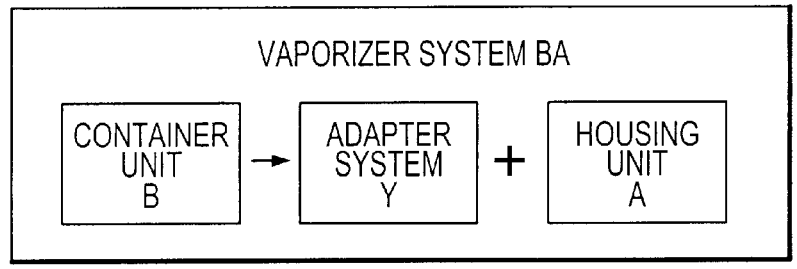
Figure 3H:
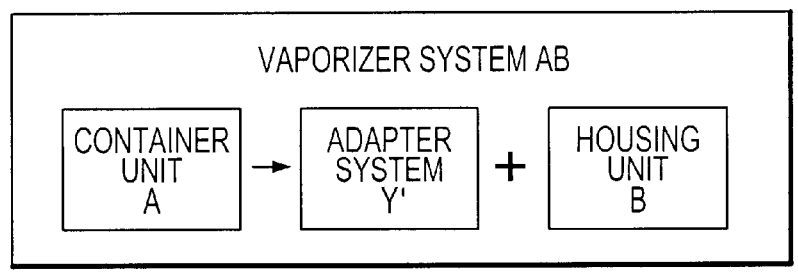

FIGS. 3G–3H demonstrate another embodiment of an adapter system of the invention. For example, adapter system Y may include an appending or attaching mechanism which when combined with housing unit A, as shown in FIG. 3G, permits receipt of container unit B, which previously did not fit into housing unit A as shown in FIG. 3C. Adapter system Y' may be used to permit receipt of container unit A into housing B as shown in FIG. 3H. Again, it should be recognized that the same adapter system may be used in both vaporizer systems A and B and, additionally, the same adapter system may be configured with shape-altering means conducive for both the container unit and the housing unit. Thus, the same adapter system may be used in any of the illustrative embodiments shown in FIGS. 3E–3H.

Figure 4:
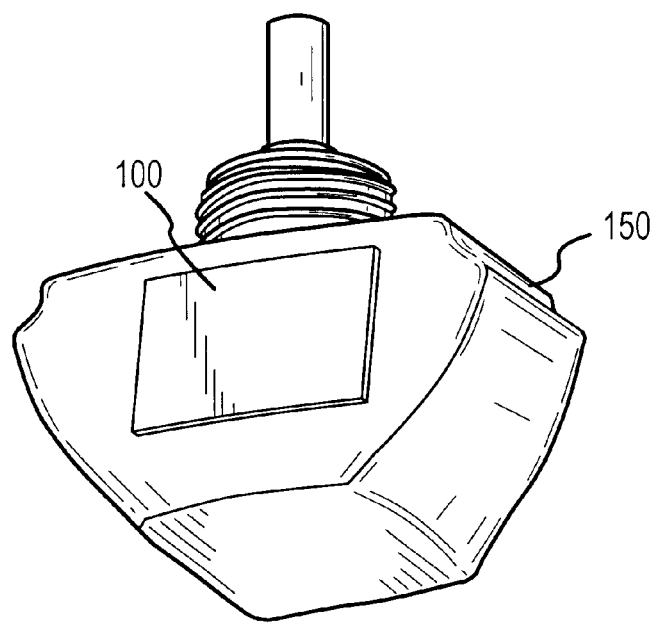
FIGS. 4–6 are various embodiments of exemplary attachment mechanisms of an adapter system in accordance with the principles of invention.
Figure 5:
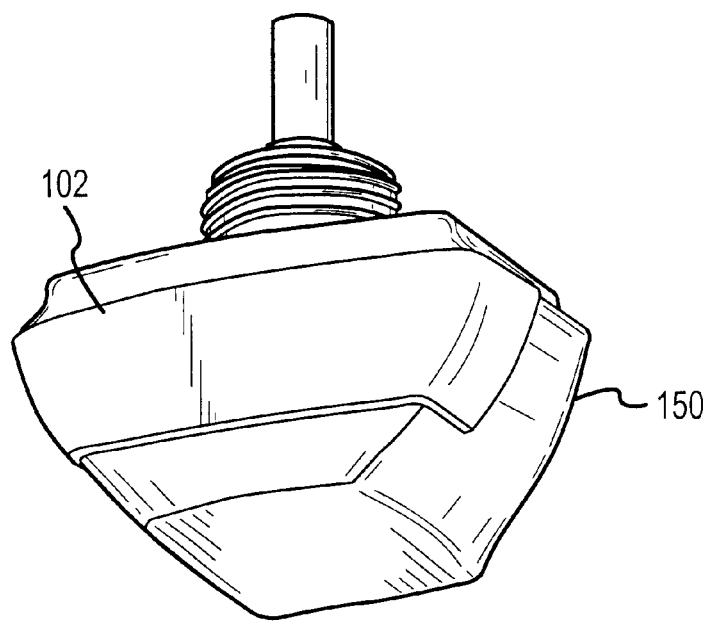
Figure 6:
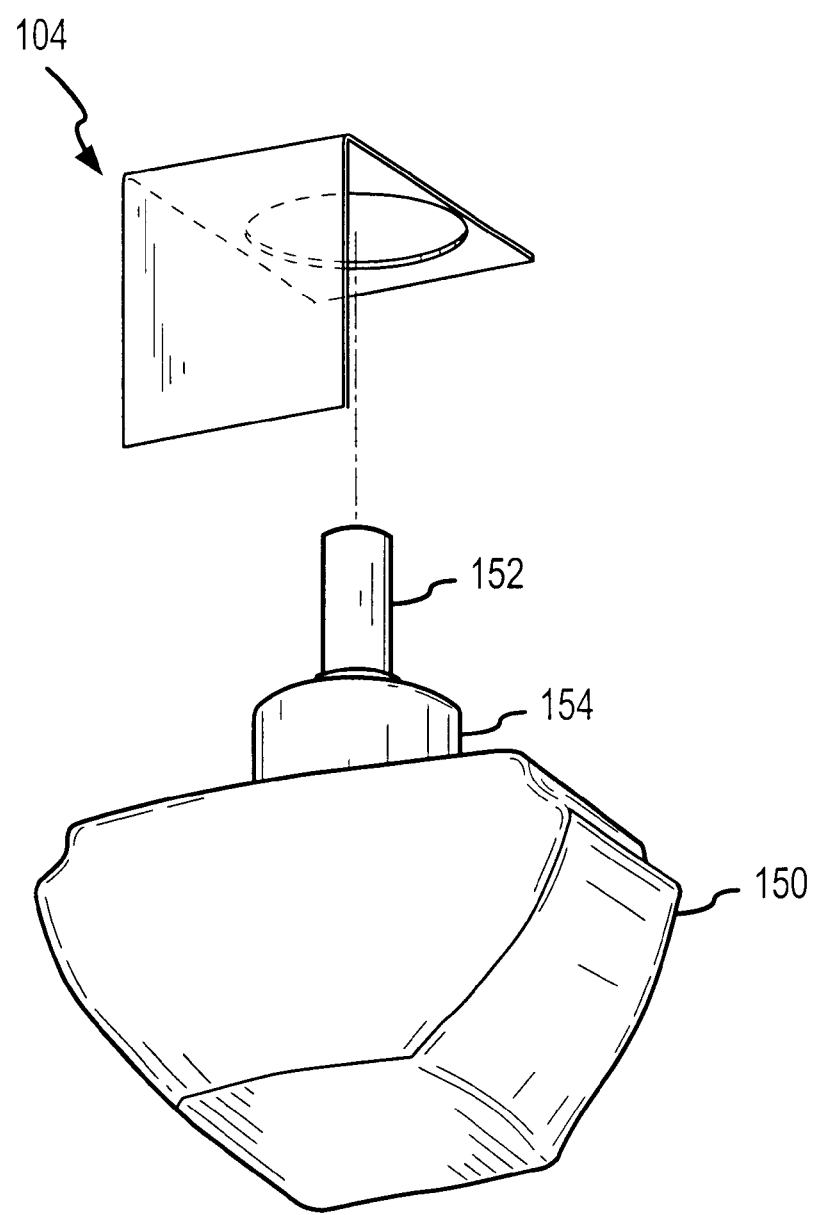

An adapter system of the invention preferably includes an appending or attaching mechanism. For example, adapter system X and X' of FIGS. 3E–3F may include an appropriate attaching mechanism for adhering or appending to a container unit, and adapter system Y and Y' of FIGS. 3G–3H may include an attaching mechanism for adhering or appending to a housing unit. With reference now to FIGS. 4–6, an adapter system having an attachment mechanism, in accordance with various exemplary embodiments of the invention, for use with a container unit 150, or the equivalent is illustrated. The following examples are not intended as a limitation on the invention but rather, are provided to fully appreciate the versatility of the invention. In the embodiment of FIG. 4, an adapter system 100 is secured to the body of container unit 150 by, for example, an adhesive source. This adhesive may be located on a back side of adapter system 100 for application to container unit 150. FIG. 5 illustrates another embodiment of an adapter system 102 for attachment about container 150. For example, adapter system 102 may include a "snap-and-fit" attachment about the body and/or neck of the container. In yet another embodiment, an adapter system 104 of FIG. 6 illustrates a "slip-on" configuration, such as over the top of the container. Although not required, it may be desirable to remove the adapter system from the container and thus the attaching mechanism may be configured to be removable or permanent. While not fully illustrated in the preceding figures, it should be appreciated that adapter systems 100–104 may also include a shape-altering means which varies the original shape of container 150 to accommodate disposal into a receptive housing unit.

Although not illustrated, it should be recognized that an adapter system of the invention may also include an attachment mechanism for use with a housing unit and may include the same or different methods of attachment as just described, e.g., an adhesive source on the adapter system may be used to attach the system within a housing unit and a "snap-and-fit" attachment within the housing unit. Moreover, an adapter system for use with a housing unit may further include a shape-altering means which varies the original shape of the housing unit to accommodate receipt of a non-conforming container.

Figure 7:
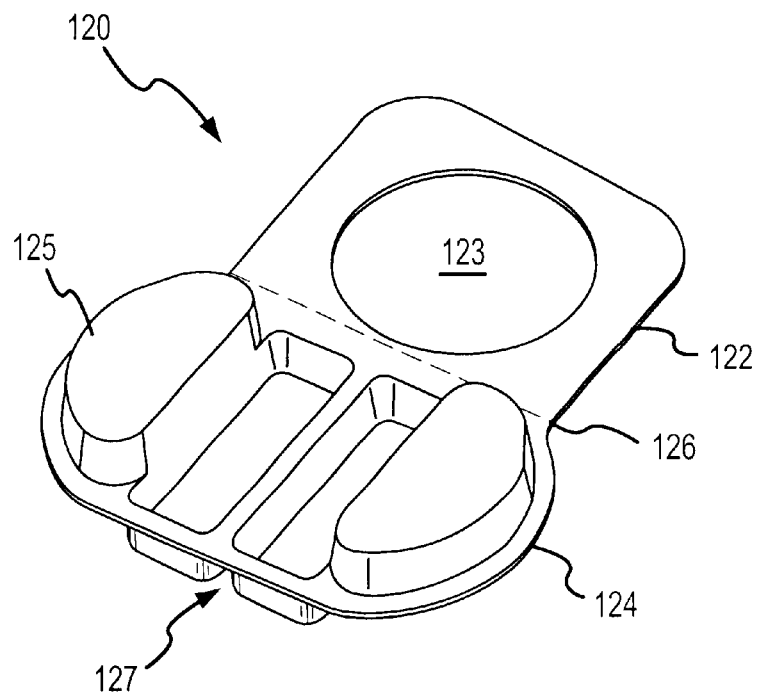
FIG. 7 is a perspective view of an adapter system in accordance with one particular embodiment of the invention.
Figure 8:
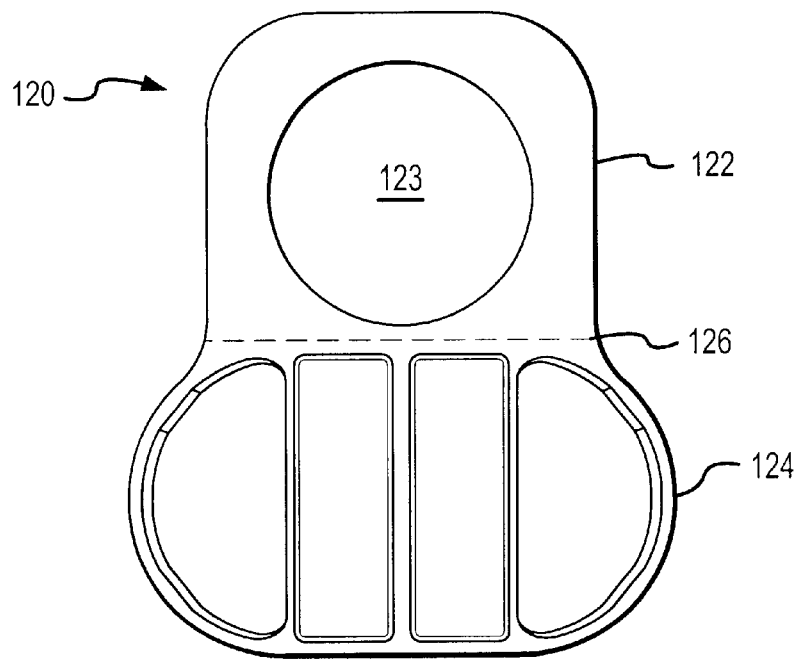
FIG. 8 is a frontal view of the adapter system of FIG. 7.

Having described the details of the invention, one specific non-limiting example of an adapter system in accordance with the general principles of the invention will now be described. The following description and accompanying figures are not intended to limit the scope of the invention in any way or manner, but are provided merely to further the general understanding of the invention. FIGS. 7 and 8 illustrate various views of an adapter system 120 according to one particular embodiment of the invention. Adapter system 120 may comprise any suitable material that is conducive to appending and form-fitting about a liquid container. For instance, flexible plastics are readily available in the industry and may be used to fabricate an inexpensive, yet durable, semi-rigid material that is easily molded to accommodate varying adapter system configurations. Preferably, adapter system 120 is conveniently sized to adequately append to a container and specifically, to a liquid vaporizer container typically for household use.

Adapter system 120 generally includes a neck portion 122, a body portion 124, and a pliable section 126 formed there between. Neck portion 122 includes an aperture 123 suitably configured for positioning about the top of a container. As shown, aperture 123 is circular in shape; however, it should be appreciated that the geometry of the neck portion, including aperture 123, may be modified for use with alternatively shaped containers. Body portion 124 is suitably configured to rest on the side of the container when neck portion 122 is placed over the container. In this manner, pliable section 126 may be folded downward to a point where body portion 124 meets the side of the container. In one particular embodiment, pliable section 126 may be fully or partially perforated to facilitate bending and/or separation of body portion 124 from neck portion 122.

Referring back to FIG. 6 and in combination with the present embodiment of FIGS. 7 and 8, an exemplary placement of adapter system 120 in connection with container 150 may be demonstrated. In operation, neck portion 122 may be suitably placed over a wick 152 and a neck 154 of container 150. Pliable section 126 is folded downward so that body portion 124 rests on the side of container 150. The positioning of neck portion 122 about neck 154 may be raised or lowered to accommodate adapter system 120 in the folded or bent position. Thus, as previously mentioned, aperture 123 may be sized to fit a variety of container neck dimensions and additionally, may be sized to fit about the entire neck 154 or alternatively to rest atop neck 154. Adapter system 120, as well as system 104, may be removed by lifting the adapter over the wick and neck region of container 150 or, in one particular embodiment, detaching body portion 124 at pliable section 126.

In this particular embodiment, the linear shape of adapter system 120 assists in manufacturing. Those of skill in the industry will readily recognize the advantages associated with having a substantially flat or linear product. For example, ease in mold casting, product packaging and shipping.

Body portion 124 may optionally include one or more suitably sized spacers 125. An adapter system of the invention may be used with a variety of container shapes and sizes, thus, depending on the particular housing unit the container is to be disposed within, the adapter system may include spacer 125 to facilitate a snug and proper fit of the container within the housing. It should be readily recognizable that the particular dimensions of spacer 125, if needed at all, generally depend on the size of the housing unit(s), and in particular, the size of the cavity within the housing unit(s). Of course, a single adapter system may be configured to provide cavity conformity to multiple housing units with the units having differently sized cavities and container guidance, attachment or retention systems. In this manner, an adapter system of the invention is universally acceptable to variously shaped containers and housing units. In general, adapter system 120, if equipped with optional spacer 125, should preferably be positioned so that spacer 125 is abutting the side of the container; however, depending upon the housing unit, adapter system 120 may be easily removed and flipped over so that spacer 125 is facing outwardly, if needed. Although described and shown in the present embodiment, it should be appreciated that any of the previously mentioned adapter systems 100–104 may also include a similar spacing mechanism.

Body portion 124 may also include an optional guidance system 127. As previously mentioned, an adapter system of the invention may be configured to append to a variety of containers and be disposed within a variety of housing units. As is generally known, some housing units often include particularly designed container guidance, attachment or retention systems, which are generally located within the cavity portion. Moreover, many of these housing units are specifically designed to accept a specially designed container having one or more corresponding guidance, attachment or retention features thereon.

Figure 2:
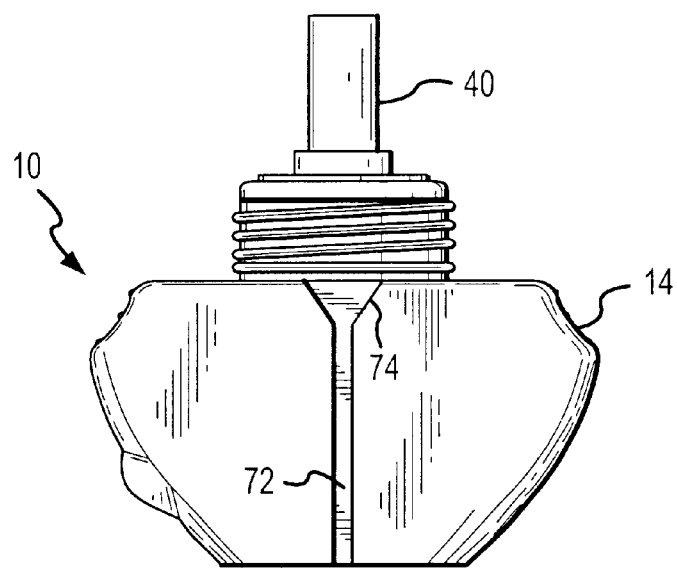

To fully understand the inclusion of additional features on exemplary adapter system 120, the following example is provided. It should be understood that the description of such is not intended to be limiting on the configuration of an adapter system of the invention, but rather is provided to further demonstrate the versatility of the invention by example. Referring again to FIGS. 1 and 2, the exemplary liquid vaporizer system disclosed in U.S. Pat. No. 6,104,867 includes a unique combination of a protrusion 70 and a recess 72 to facilitate guidance of bottle unit 14 within cavity 26 of housing unit 12. With combined reference now to FIGS. 7 and 8, adapter system 120 includes a similar guidance system 127, and specifically a recess similar to recess 72 that properly fits within protrusion 70. In operation, adapter system 120 may be suitably placed over the neck of a container (e.g., a container or bottle unit such as container 150 not specifically designed to fit within cavity 26 of housing unit 12) and folded at pliable section 126 so that body portion 124 rests on the side of the container. Neck portion 122 should preferably be placed so that guidance system 127 is in a receptive position when brought in contact with protrusion 70. In this particular embodiment, guidance system 127 should be facing in an outwardly direction so that the recess of guidance system 127 can suitably complement protrusion 70. The otherwise non-conforming container (e.g., container 150) is transposed by the appendage of adapter system 120 and may now be disposed within cavity 26 of housing unit 12 without jeopardizing the intended performance or fit of either housing unit 12 or the non-conforming container.

In another embodiment, an adapter system in accordance to the principles of the invention is pre-formed in the bent or folded position, therefore obviating a pliable section. For example, in this particular embodiment, the adapter system may be molded in the folded position (e.g., as shown on FIGS. 5 and 6). This embodiment may have particular use for specific container shapes and/or cavity dimensions of certain housing units.

An adapter system of the present invention has been described above with reference to various exemplary embodiments. However, those skilled in the art will readily recognize that changes and modifications may be made to the embodiments without departing from the scope of the invention. For example, the adapter system may be configured to append to a container, a housing unit, or both. The shape-altering means may be configured for disposal into a particular housing unit, a plurality of differently shaped housing units or for receipt by a particular container unit or a plurality of container units. The adapter system may be void of spacers and/or guidance systems. Alternatively, the body portion may include various additions of container retention, attachment and stabilization systems. The overall configuration and shape of the adapter system may be modified to adhere to a specific housing unit, container unit or combination of both, without departing from the spirit of the invention. Although conveniently described in connection with liquid containers or refill bottle units, the invention has general applicability to other vaporizing devices as well which may utilize a gel, solid or various other volatile substances. These and other changes or modifications are intended to be included within the scope of the invention as set forth in the appended claims.

We claim:

1. A refill bottle system for use in a vaporizing device, said system comprising:
   a liquid container having a shape that is non-conforming to said vaporizing device; and
   an adapter coupled to said liquid container and altering the shape of said liquid container, wherein said refill bottle system permits said otherwise non-conforming liquid container to be used in said vaporizing device, said adapter having:
   a body portion;
   a neck portion; and
   a pliable section between said neck and body portions, said pliable section permitting said body portion to contact a side of said container.

2. The adapter of claim 1, wherein said pliable section comprises perforation.

3. The adapter of claim 1 being removably appended to said liquid container.

4. The adapter of claim 1, wherein said neck portion is coupled about a neck of said container.

5. The adapter of claim 1, said adapter comprising a shape-altering spacer.

6. The adapter of claim 1, said adapter comprising a shape-altering guidance system.

7. A method of vaporization including a vaporizer of the type having a housing unit and a container unit, the method comprising:
   appending a neck portion of an adapter system to a neck of a non-disposing container; and
   disposing said container and said adapter system within said housing unit, wherein said adapter system modifies the shape of said container to permit disposition of said non-disposing container.

8. The method of claim 7, further comprising bending said adapter system to a near right angle.

9. The method of claim 7, wherein said appending step comprises adhering said adapter system to said non-disposing container.

10. The method of claim 7, further comprising:
    removing said non-disposing container and said adapter system from said housing unit; and
    removing said adapter system from said non-disposing container.

11. An adapter for a liquid vaporizer container, said adapter comprising:
    an attachment mechanism for coupling to said container, said attachment mechanism comprises a neck portion having an aperture configured to fit about said container;
    a shape-altering mechanism to modify a shape of said container to conform for disposal into a liquid vaporizer system.

12. The adapter of claim 11, wherein said attachment mechanism comprises attachment to said liquid vaporizer system prior to disposal of said container.

13. The adapter of claim 11, wherein said shape-altering mechanism comprises one or more spacers.

14. The adapter of claim 11, wherein said shape-altering mechanism comprises a guidance system corresponding to a reciprocating guidance system of said liquid vaporizer system.

* * * * *